United States Patent
Siochi et al.

[11] Patent Number: 6,142,925
[45] Date of Patent: Nov. 7, 2000

[54] METHOD AND SYSTEM FOR INCREASING RESOLUTION IN A RADIOTHERAPY SYSTEM

[75] Inventors: Ramon Alfredo Carvalho Siochi, Fairfield; John Hughes, Martinez, both of Calif.

[73] Assignee: Siemens Medical Systems, Inc., Iselin, N.J.

[21] Appl. No.: 09/233,977

[22] Filed: Jan. 20, 1999

[51] Int. Cl.[7] .................................................. A61N 5/00
[52] U.S. Cl. ................................................................ 600/1
[58] Field of Search ............................ 600/1–8; 128/897, 128/898

[56] References Cited

U.S. PATENT DOCUMENTS

| | | |
|---|---|---|
| 5,202,565 | 4/1993 | Torii ........................................ 250/327.2 |
| 5,538,494 | 7/1996 | Matsuda ........................................ 600/1 |
| 5,663,999 | 9/1997 | Siochi ........................................ 378/65 |
| 6,024,689 | 2/2000 | Castle et al. ................................ 600/1 |

Primary Examiner—Max Hindenburg

[57] ABSTRACT

Method and system aspects for increasing resolution of a radiotherapy system to achieve virtual fractional monitor unit radiation delivery are described. Included in a method aspect, and system for achieving same, is identification of a desired treatment dose, the desired treatment dose exceeding a resolution of a radiation treatment device. Further included is the development of a schedule of treatment sessions for delivering the desired treatment dose by the radiation treatment device that produces a combined treatment dose equaling the desired treatment dose without exceeding the resolution within each treatment session.

26 Claims, 2 Drawing Sheets

METHOD AND SYSTEM FOR INCREASING RESOLUTION IN A RADIOTHERAPY SYSTEM

FIELD OF THE INVENTION

The present invention relates to radiation treatment devices, and more particularly, to increasing the dosimetry resolution of a radiotherapy system.

BACKGROUND OF THE INVENTION

Radiation-emitting devices are generally known and used for radiation therapy in the treatment of patients, for example. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. During treatment, the radiation beam is provided on one zone of a patient lying in the isocenter of gantry rotation.

The delivery of radiation by a radiation therapy device is normally prescribed and approved by an oncologist with administration by a therapist. Typical therapy involves programming the device by the therapist to deliver the radiation beam from the linear accelerator at a known and constant rate of a chosen number of monitor units per time period, (e.g., MU/minute), where a monitor unit generically refers to a dose unit of radiation for a chosen calibration and indicates the resolution of the radiation therapy device. With the resolution preset, changes to increase the resolution are difficult without altering the linear accelerator hardware/firmware, which is both expensive and time-consuming. For example, in some situations, it may be determined that a fractional number of monitor units are desired for a particular treatment plan, but the available radiation treatment device may only have a resolution of a single monitor unit. In such situations, the desired treatment dose cannot be delivered as precisely as is preferred.

Therefore, what is needed is a manner of effectively increasing the resolution of a radiation therapy device without altering the linear accelerator hardware/firmware.

SUMMARY OF THE INVENTION

The present invention provides method and system aspects for increasing resolution of a radiotherapy system to achieve virtual fractional monitor unit radiation delivery. Included in a method aspect, and system for achieving same, is identification of a desired treatment dose, the desired treatment dose exceeding a resolution of a radiation treatment device. Further included is the development of a schedule of treatment sessions for delivering the desired treatment dose by the radiation treatment device that produces a combined treatment dose equaling the desired treatment dose without exceeding the resolution within each treatment session.

Through the present invention, a mixture of monitor unit settings separated by the monitor unit resolution on varying days is delivered to allow a patient to effectively receive the average of these settings, thus achieving a higher monitor unit resolution. With the present invention, expensive and time-consuming alterations to linear accelerator hardware/firmware are advantageously avoided. Additionally, regardless of a resolution, the aspects of the present invention allow the resolution to be taken a tenth further, thus increasing resolution to deliver virtual fractional monitor unit doses. These and other advantages of the aspects of the present invention will be more fully understood in conjunction with the following detailed description and accompanying drawings.

DETAILED DESCRIPTION OF THE INVENTION

The present invention relates to achieving a higher monitor unit resolution in a radiotherapy system. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field of a patient, and for delimiting the field using at least one movable plate in the beam path from a radiation source. This is by way of example. Thus, the present invention is not intended to be merely limited to the embodiment shown but is to be accorded the widest scope consistent with the principles and features described herein.

Figure 1:
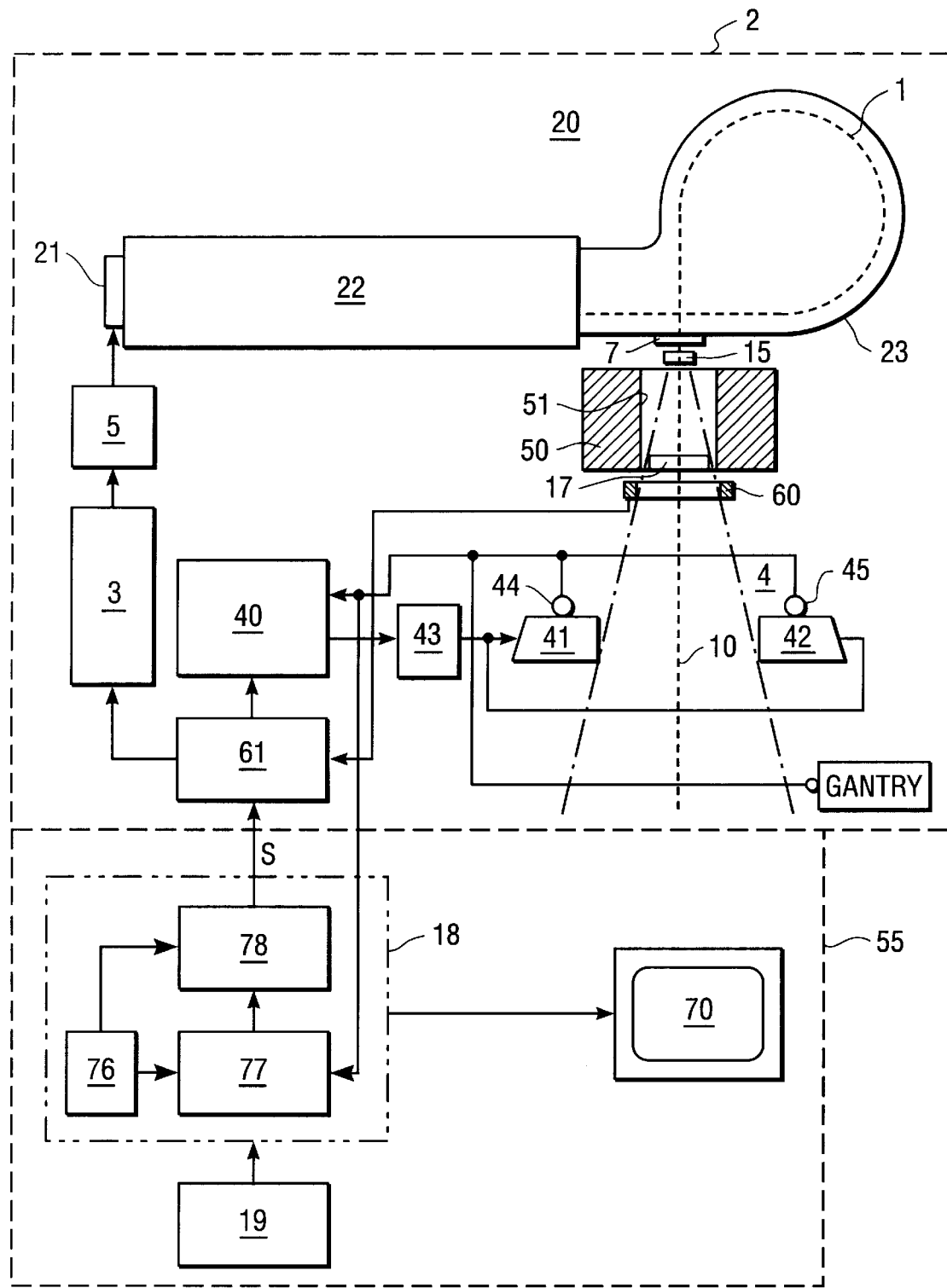
FIG. 1 is a block diagram illustrating portions of a processing unit, control unit, and a beam generation system in a radiation treatment device for a preferred embodiment of the present invention.

FIG. 1 shows a portion of an illustrative radiotherapy system including radiation treatment device 2 and portions of a treatment processing unit in detail. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, in which the dose is ascertained. If the scattering foils are replaced by a target, the radiation beam is an X-ray beam.

Figure 2:
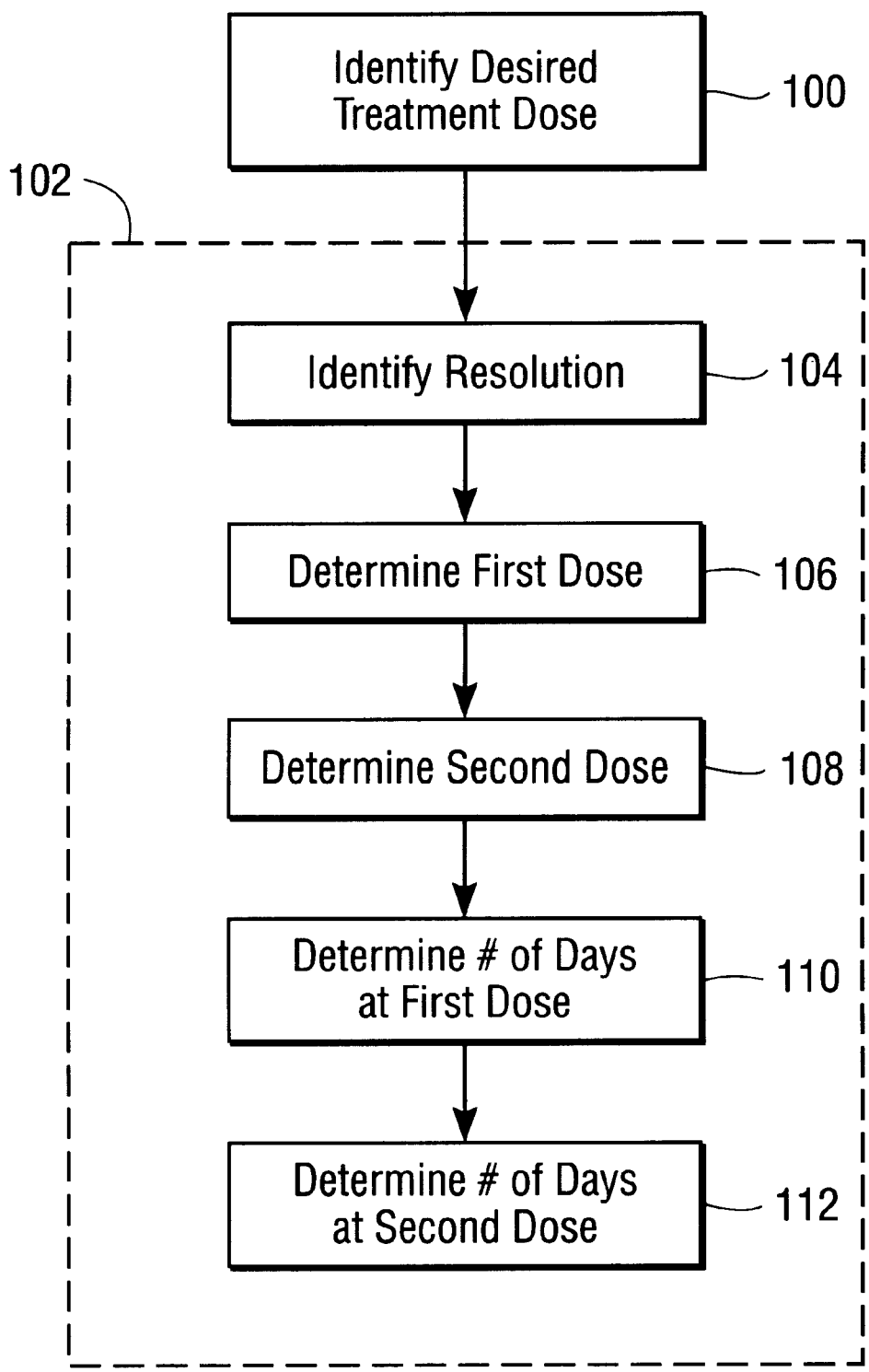
FIG. 2 illustrates a flow diagram of a process for increasing resolution of a radiotherapy system in accordance with a preferred embodiment of the present invention.

Plate arrangement 4 comprises a pair of aperture plates 41 and 42 and an additional pair of aperture plates (not shown) arranged perpendicular to plates 41 and 42. In order to change the size of the irradiated field, the aperture plates 41 and 42 can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions.

The area of a patient that is irradiated is known as the field. As is well known, plates 4 are substantially impervious to the emitted radiation. They are mounted between the radiation source and patient in order to delimit the field. Areas of the body, for example, healthy tissue, are therefore subjected to as little radiation as possible, and preferably to none at all. As previously described, with at least one of the plates movable, the distribution of radiation over the field need not be uniform (one region can be given a higher dose than another); further, with the gantry able to be rotated, different beam angles and radiation distributions are allowed without having to move the patient around.

A central treatment processing 55 is usually located apart from radiation treatment device 2 in a different room to protect the therapist from radiation. Treatment processing unit includes an output device, such as at least one visual display unit or monitor 70, and an input device, such as a keyboard 19, although data can be input also through data carriers, such as data storage devices. The treatment processing unit is typically operated by the therapist who administers actual delivery of a radiation treatment as prescribed by an oncologist. By utilizing keyboard 19, or other input device, the therapist enters into a control unit 76 of the treatment processing unit the data that defines the radiation to be delivered to the patient. On the screen of a monitor 70, various data can be displayed before and during the treatment.

Central processing unit 18, included in treatment processing unit, is connected with the input device, e.g., keyboard 19, for inputting the prescribed or desired treatment dose of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78, which receives signals from the control unit 76 and memory 77 for combination to produce a set signal, S, that identifies a dose rate for dose rate control unit 61.

As previously mentioned, the dose unit capable of being delivered by the a trigger system 3, as controlled by way of the treatment processing unit including the control unit 76, is identified as a monitor unit value, which indicates the resolution of the radiation treatment device 2. In accordance with the present invention an effective increase in a given resolution is achieved by delivering a mixture of monitor unit settings separated by the monitor unit resolution on alternating days of treatment. FIG. 2 illustrates a flow diagram representative of a preferred method of increasing the resolution. The process begins with identification of the desired treatment dose (A) as one that exceeds the resolution of the radiation treatment device (step 100). To produce the desired treatment dose, the present invention develops a schedule of treatment sessions for delivering the radiation at a combined treatment dose that matches the desired treatment dose without exceeding the resolution within each treatment session, as represented by the steps within box 102 of FIG. 2. A treatment session for this discussion refers to delivery of a particular dose over a determined number of days.

Thus, the development of a schedule includes the identification of the resolution of the treatment system (R) (step 104). Also included is a determination of a first dose (A1) (step 106). In accordance with a preferred embodiment, the first dose is calculated as follows: $A1=R*Int(A/R)$; i.e., the first dose is equal to the resolution value multiplied by the integer portion of the division of the desired treatment dose by the resolution value. Further included in developing a schedule is a determination of a second dose (A2) (step 108). The second dose is suitably calculated as $A2=A1+R$; i.e., a sum of the first dose and the resolution value. The schedule development then continues with a determination of the number of days (D1) of treatment at the first dose (step 110), and the number of days (D2) of treatment at the second dose (step 112).

In determining the number of days at each dose level, preferably a rational number (F) is calculated by subtracting the first dose from the total dose and dividing the result by the resolution, i.e., $F=(A-A1)/R$. The rational number represented by F is equated to a first integer, m, divided by a second integer, n, i.e., $F=m/n$. The first number of days, D1, then results from a subtraction of the first integer from the second integer, i.e., $D1=(n-m)$, while the second number of days, D2, equals the first integer, i.e., $D2=m$. A resolution of $R/n$ is achieved through the present invention by radiating the patient with A1 monitor units on D1 days, and A2 monitor units on D2 days.

By way of example, if the resolution R of a particular radiation treatment device is 1 monitor unit (MU) and a desired treatment dose is 7.33 MUs, then $A1=1*Int(7.33/1)=7$. To determine A2, A1 is added to R, i.e., $A2=7+1=8$. The values for the number of first and second days D1 and D2 then proceeds. Thus, rational number F is determined to determine the values for 'm' and 'n'. E.g., $F=(A-A1)/R=(7.33-7)/1=0.33$, which is approximately ⅓. Thus, m=1 and n=3, so that $D1=n-m=3-1=2$, and $D2=m=1$. In accordance with the present invention for this example, a scheduled delivery results where 7 MUs are delivered on two out of three days, and 8 MUs are delivered on the third day. The treatment sessions of two days at 7 MUs and one day at 8 MUs are performed for every set of three days of treatment and result in an average of the settings over the three days that equals the desired 7.33 MUs. As shown by this example, the present invention increases the resolution to achieve virtual fractional monitor unit radiation delivery.

As a further example, a schedule for a desired treatment dose of 5.15 MUs with a radiation treatment device having a resolution of 0.1 MUs is developed. Thus, R=0.1; A=5.15; so $A1=0.1*Int(5.15/0.1)=5.1$; $A2=A1+R=5.1+0.1=5.2$; and $F=(A-A1)/R=(5.15-5.1)/0.1=0.5$, which is represented as ½, so that m=1, and n=2. Therefore, $D1=n-m=2-1=1$, and $D2=m=1$. From the preferred embodiment, a scheduled delivery having 5.1 MUs delivered on one out of every two days, and 5.2 MUs delivered on the other of the two days results, thus effectively increasing the resolution of the radiation treatment device.

In utilizing the present invention in the radiation treatment device 2, various manners of monitoring the treatment sessions may be performed. For example, calendar features may be utilized to view and/or print the developed schedule, such as with the calendar features of LANTIS available from Siemens Corp., New Jersey. Alternatively, the treatment schedule may be set up via a treatment programming procedure, such as PRIMEVIEW, also available from Siemens Corp. A user interface may also be used to visually indicate the virtual monitor units delivered on a daily basis during treatment, along with a cumulative total of the MUs actually delivered to date. For example, if the desired treatment dose of MUs to be delivered is 10.5, with 10 MUs delivered on one day and 11 MUs delivered on a next day, the number of virtual monitor units delivered may be displayed appropriately as 10.5 on the first day with a cumulative total displayed as 10. On the second day, the number of virtual monitor units may also be displayed as 10.5, with a cumulative total displayed as 21.

A further feature of radiation therapy involves portal images, which are commonly used in radiation therapy to verify and record the patient tumor location. Portal images include manual (film) and electronic images (EPI) taken before or after the treatment. Normally, a set number of monitor units are delivered during the taking of the portal image. The present invention is suitably adjusted to take into account the contribution of the radiation supplied during the portal imaging. For example, once the desired treatment dose is identified, a determination of a need to account for a portal imaging MU contribution is made. If no contribution exists, the process proceeds as described above with reference to FIG. 2. However, if a contribution does exist, the MUs required for the portal imaging are deducted from the desired treatment dose. The remaining total MUs over the whole treatment course can then be divided up over the number of days for treatment, and the resulting MUs per treatment can be developed in accordance with the preferred procedure described with reference to FIG. 2.

In addition, conventional radiation therapy technique typically utilize field sizes in the range of 5 to 30 cm, and doses per fraction in the range of 70 to 200 MU (monitor units). With intensity modulation techniques (IMRT), treatment fields and doses are calculated to be more geometrically and dosimetrically precise. Treatment fields are decomposed into dose segments, which are smaller than in conventional treatments. A description of segmentation of the treatment field is provided in U.S. Pat. No. 5,663,999 entitled "Optimization of an Intensity Modulated Field". In situations where the treatment field is segmented, such as by techniques described in U.S. Pat. No. 5,663,999, contributions to the MUs from portal imaging are preferably accounted for during the segmentation. When portal imaging is used, the effect of one or more port film MUs can be subtracted from a set of IMRT fields for which a new intensity map is then calculated. The process of increasing the resolution to provide virtual fractional monitor unit delivery within each of the segments may then be achieved by application of the aspects of the present invention as described hereinabove with reference to FIG. 2.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for effectively increasing resolution of a radiotherapy system, the method comprising:
    identifying a desired treatment dose, the desired treatment dose exceeding a resolution of a radiation treatment device; and
    developing a schedule of treatment sessions for delivering the desired treatment dose by the radiation treatment device that produces a combined treatment dose equaling the desired treatment dose without exceeding the resolution within each treatment session.

2. The method of claim 1 wherein developing a schedule further comprises identifying the resolution of the radiation treatment device.

3. The method of claim 2 further comprising determining a first dose.

4. The method of claim 3 wherein determining a first dose further comprises multiplying the resolution by an integer portion of a result of dividing the desired treatment dose by the resolution.

5. The method of claim 3 further comprising determining a second dose.

6. The method of claim 5 wherein determining a second dose further comprises summing the first dose and the resolution.

7. The method of claim 5 further comprising determining a first number of days at the first dose and a second number of days at the second dose.

8. The method of claim 7 wherein determining further comprises subtracting the first dose from the desired treatment dose and dividing by the resolution to provide a rational number.

9. The method of claim 8 wherein the rational number represents a first integer value divided by a second integer value.

10. The method of claim 9 wherein the first number of days comprises the second integer value reduced by the first integer value, and the second number of days comprises the first integer value.

11. A radiotherapy system with increased dose unit resolution, the system comprising:
    a radiation treatment device, the radiation treatment device delivering radiation at a set resolution; and
    a treatment processing unit coupled to the radiation treatment device and including a control unit for identifying a desired treatment dose, the desired treatment dose exceeding the set resolution, and for developing a schedule of treatment sessions for delivering the desired treatment dose that produces a combined treatment dose equaling the desired treatment dose without exceeding the set resolution within each treatment session.

12. The system of claim 11 wherein treatment processing unit develops the schedule by identifying the resolution of the radiation treatment device.

13. The system of claim 12 wherein the treatment processing unit further determines a first dose.

14. The system of claim 13 wherein the first dose further comprises a result of multiplying the resolution by an integer portion of a division of the desired treatment dose by the resolution.

15. The system of claim 13 wherein the treatment processing unit further determines a second dose.

16. The system of claim 15 wherein the second dose further comprises a combination of the first dose and the resolution.

17. The system of claim 15 wherein the treatment processing unit further determines a first number of days at the first dose and a second number of days at the second dose.

18. The system of claim 17 wherein the treatment processing unit further subtracts the first dose from the desired treatment dose and divides by the resolution to provide a rational number.

19. The system of claim 18 wherein the rational number represents a first integer value divided by a second integer value.

20. The system of claim 19 wherein the first number of days comprises the second integer value reduced by the first integer value, and the second number of days comprises the first integer value.

21. A method for effectively increasing dose unit resolution of a radiotherapy system, the method comprising:

(a) identifying a desired treatment dose, the desired treatment dose exceeding a resolution of a radiation treatment device;
(b) identifying the resolution of the radiation treatment device;
(c) determining a first dose based on the resolution and the desired treatment dose;
(d) determining a second dose based on the resolution and the first dose;
(e) determining a first number of days at the first dose; and
(f) determining a second number of days at the second dose, wherein the delivery of the first dose for the first number of days and delivery of the second dose for the second number of days provides the desired treatment dose.

22. The method of claim 21 wherein the first dose and second dose are within the resolution of the radiation treatment device.

23. The method of claim 21 wherein determining a first dose further comprises multiplying the resolution by an integer portion of a result of dividing the desired treatment dose by the resolution, and determining a second dose further comprises combining the first dose and the resolution.

24. The method of claim 21 wherein determining the first number of days and the second number of days further comprises subtracting the first dose from the desired dose and dividing by the resolution to provide a rational number, the rational number representing a first integer value divided by a second integer value.

25. The method of claim 24 wherein the first number of days comprises the second integer value reduced by the first integer value, and the second number of days comprises the first integer value.

26. The method of claim 21 further comprises determining whether a portal imaging dose needs to be accounted for in the desired treatment dose, wherein when a portal image dose does need to be accounted for, the method further comprises reducing the total desired treatment dose by the portal imaging dose, dividing the reduced total desired treatment dose by the number of treatment days to yield a new daily treatment dose and performing the steps (a)–(f) for the new daily treatment dose.

* * * * *